(12) United States Patent
Pitt et al.

(10) Patent No.: US 7,240,572 B2
(45) Date of Patent: Jul. 10, 2007

(54) VACUUM ASSISTED AFFINITY CHROMATOGRAPHY DEVICE AND METHOD

(75) Inventors: Aldo M. Pitt, Wayland, MA (US); Gary LaBombard, Concord, NH (US); Phillip Clark, Wakefield, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 11/051,047

(22) Filed: Feb. 4, 2005

(65) Prior Publication Data

US 2005/0178216 A1    Aug. 18, 2005

Related U.S. Application Data

(60) Provisional application No. 60/545,671, filed on Feb. 18, 2004.

(51) Int. Cl.
*G01N 1/00* (2006.01)
(52) U.S. Cl. .................................... 73/863.21
(58) Field of Classification Search ............ 73/863.21, 73/61.55, 61.56, 23.41, 23.42; 210/656, 210/198.2; 422/70, 101; 95/82; 96/101, 96/106, 107
See application file for complete search history.

(56) References Cited

U.S. PATENT DOCUMENTS

| | | | | |
|---|---|---|---|---|
| 3,063,286 A | * | 11/1962 | Nerheim ..................... 73/23.41 |
| 3,630,683 A | * | 12/1971 | Robb ........................... 422/70 |
| 3,731,466 A | * | 5/1973 | Kunsman et al. ............. 96/106 |
| 3,953,172 A | * | 4/1976 | Shapiro et al. .............. 436/500 |
| 4,213,326 A | * | 7/1980 | Brodasky .................... 73/23.37 |
| 4,422,941 A | * | 12/1983 | Vaughan et al. ............ 210/657 |
| 4,427,415 A | | 1/1984 | Cleveland .................... 436/57 |
| 4,755,301 A | | 7/1988 | Bowers ....................... 210/650 |
| 4,871,662 A | * | 10/1989 | Rosov .......................... 435/30 |
| 5,092,218 A | * | 3/1992 | Fine et al. ...................... 86/50 |
| 5,238,556 A | | 8/1993 | Shirkhan .................. 210/198.2 |
| 5,375,477 A | | 12/1994 | Neill et al. .............. 73/863.23 |
| 5,413,708 A | * | 5/1995 | Huse et al. .............. 210/198.2 |
| 5,447,079 A | * | 9/1995 | Neill et al. .............. 73/863.23 |
| 5,601,711 A | * | 2/1997 | Sklar et al. ................. 210/238 |
| 5,603,899 A | | 2/1997 | Franciskovich et al. .... 422/100 |
| 5,783,087 A | | 7/1998 | Vlock et al. ................ 210/651 |
| 5,911,954 A | * | 6/1999 | Ford et al. .................. 422/101 |

(Continued)

FOREIGN PATENT DOCUMENTS

EP      1 206 483      7/2003

(Continued)

*Primary Examiner*—Robert Raevis
(74) *Attorney, Agent, or Firm*—Nields & Lemack

(57) ABSTRACT

Sample preparation device and method particularly useful for large volume capture and small volume elution. The device comprising a manifold, a sample holder or reservoir, and a filter unit containing chromatography media such that a filtration path is established between the sample holder, the filter unit and the manifold. Upon subjecting the sample in the sample holder to a driving force such as vacuum, the sample flows through the chromatography media in the filter unit. Molecules of interest bind to the media and any unwanted molecules can be washed under vacuum mode. Elution can then be carried out by removing the filter unit and subjecting the media to a driving force such as vacuum or centrifugation. In another embodiment, molecules of interest can be eluted into a low volume centrifugal spinner directly in the manifold.

13 Claims, 3 Drawing Sheets

U.S. PATENT DOCUMENTS

| | | | |
|---|---|---|---|
| 5,976,824 A | 11/1999 | Gordon | 435/29 |
| 5,981,736 A | 11/1999 | Coffman | 536/25.4 |
| 6,156,196 A * | 12/2000 | Gao | 210/198.2 |
| 2002/0102563 A1 | 8/2002 | Gjerde et al. | 435/6 |
| 2002/0110495 A1 | 8/2002 | Hunt et al. | 422/101 |
| 2003/0069413 A1* | 4/2003 | Pai et al. | 536/25.4 |
| 2004/0154969 A1* | 8/2004 | Thompson | 210/198.2 |
| 2005/0016263 A1* | 1/2005 | Yamauchi et al. | 73/61.56 |

FOREIGN PATENT DOCUMENTS

| | | |
|---|---|---|
| WO | 02/16580 | 2/2002 |

* cited by examiner

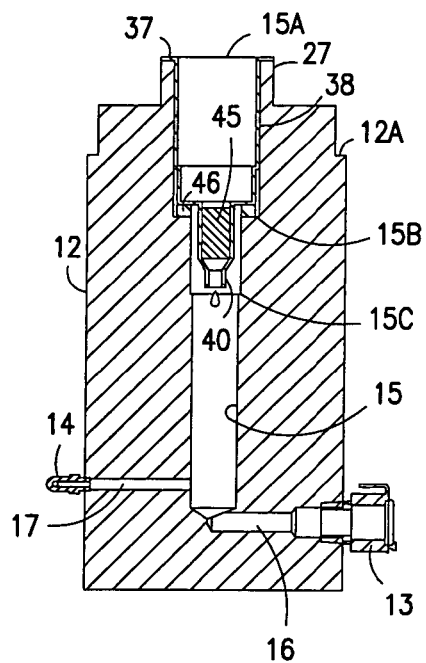 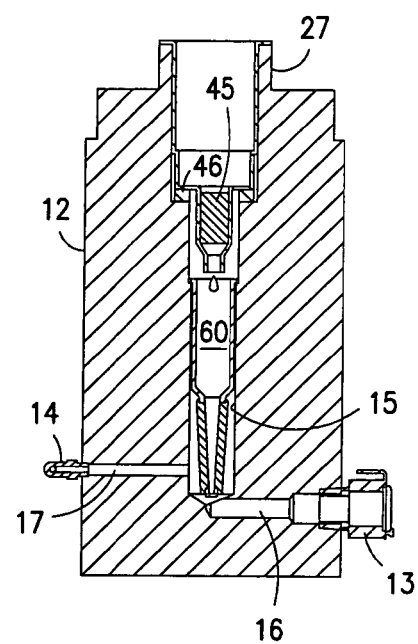
FIG. 4  FIG. 5
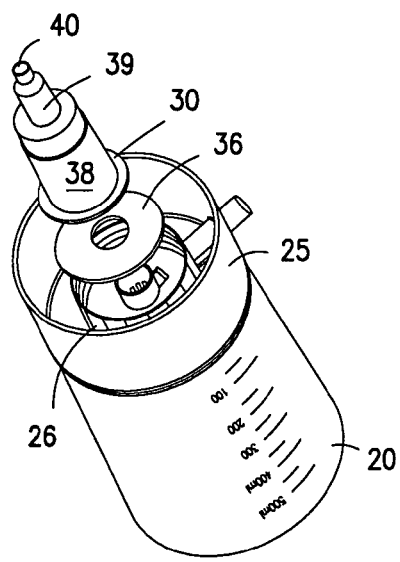 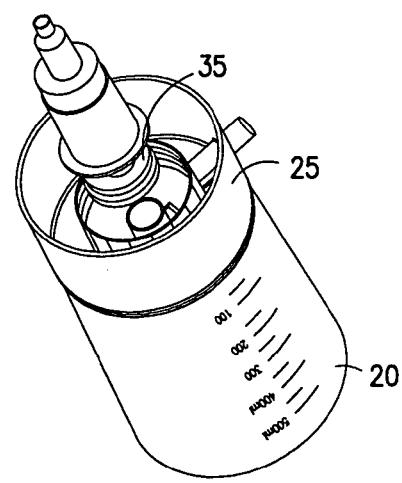
FIG. 6  FIG. 7

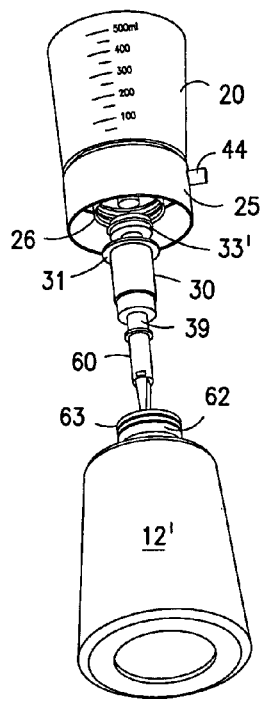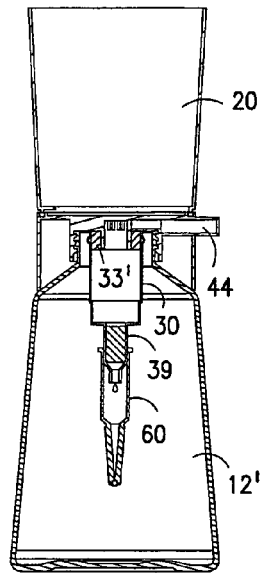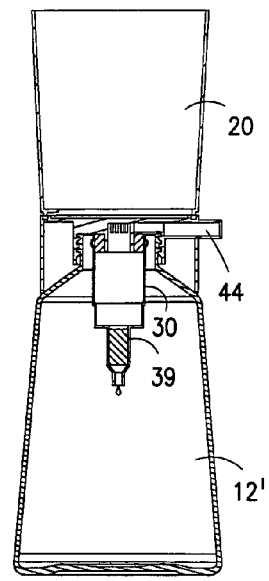
FIG. 8  FIG. 9  FIG. 10
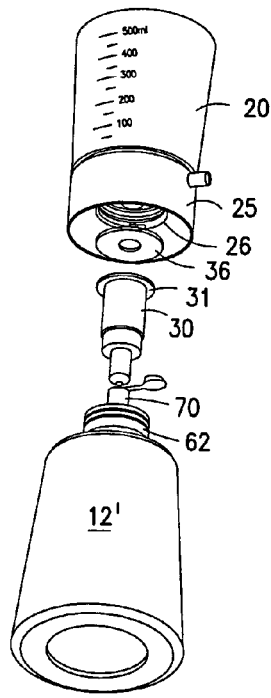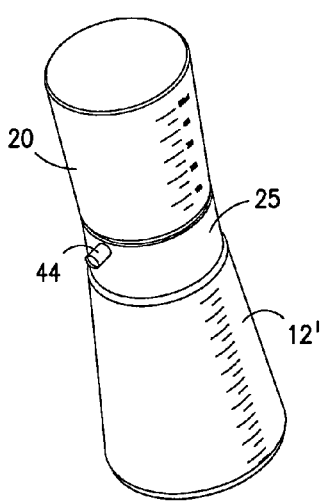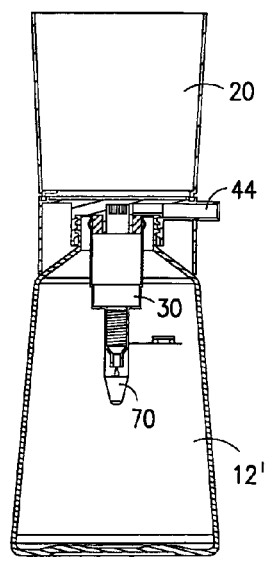
FIG. 11  FIG. 12  FIG. 13

VACUUM ASSISTED AFFINITY CHROMATOGRAPHY DEVICE AND METHOD

This application claims priority of U.S. Provisional Application Ser. No. 60/545,671 filed Feb. 18, 2004, the disclosure of which is incorporated herein by reference.

BACKGROUND OF THE INVENTION

Numerous laboratory devices have been developed to carry out filtration, chromatography and centrifugation in order to concentrate, separate and/or purify laboratory samples.

Researchers routinely need to concentrate their sample prior to other investigative research. There are two primary approaches to sample concentration: specific capture, (chromatography resin and affinity chemistries) or size exclusion filters.

For researchers using size exclusion filters, there are limitations they must accommodate in their work. The format of these devices can be either small sample volume centrifugal filters or preparative scale tangential flow separation systems. The preparation systems typically include pumps and gauges and require the user to be skilled and to monitor the process during the separation. A further limitation for the preparative systems is that the final concentrate volume can be larger (50 or more mls). Considering that the researcher's starting sample may be 250 to 1000 mls, a 50 mls concentrate is a low concentration factor. The centrifugal devices are small in scale and the sample they can conveniently process is small (less then 100 ml) because of the size limitations of the centrifuge rotor. The centrifuge devices can achieve very high concentration factors, 100× is not uncommon, but the small starting volume would require the research to monitor the separation and repeatedly refill the filter unit to concentrate the entire starting sample.

In some cases, the centrifuge device is prepared with a packed column of separation media, chromatography or affinity. These devices similarly suffer by starting volume limitations and require repeated fillings to concentrate samples greater than 100 mls.

The same limitation for process UF applies to the preparative scale chromatography media systems, in which high cost for pumps and gauges and skilled operators are required and final concentrate volumes are larger than desired.

Another low cost approach to specific capture systems is to use gravity columns. When using these systems, the researcher has to set up the system so as to achieve a head pressure sufficient to process the sample through the column. This is achieved by placing the sample to be processed in a tank and positioning it above the separation column. Tubes and connectors are used to assemble the typical gravity set up. These set ups may be inexpensive to run, but a major limitation is the processing time which can be long enough so as to require that the process be performed in a cold room to protect the sample from thermal degradation.

U.S. Pat. No. 4,755,301 discloses a centrifugal method and apparatus for concentrating macromolecules without filtering to dryness. A semi-permeable ultrafiltration membrane separates a sample reservoir from a filtrate cup, and filtrate ducts below the membrane are offset sufficiently inward from the edge of the membrane so that when the apparatus is used in a fixed angle centrifuge rotor, filtration stops once the retentate meniscus reaches the centrifugal radial level of the outermost edge of the outermost filtrate duct.

Conventional sample preparation devices are limited to relatively small sample volumes, generally about 0.5-80 milliliters.

These devices have had chromatography media added to them, typically by removing the membrane and replacing it with a more openly porous filter or frit and adding the chromatography media upstream of that filter. In some instances, a top layer of frit may be used to hold the media in the tube during storage and handling. A small sample containing a mixture of components including the desired component (generally a peptide or protein) is added to the sample reservoir and the device is then centrifuged. The desired component typically binds (is captured) to the selected media and all other material and fluid passes through the device to the filtrate reservoir. The device is removed, the filtrate is either dumped or used in further testing and a wash solution is added to the device that removes any unbound material that may have been trapped between the media or left on the surface as the fluid level dropped. This device is removed, the filtrate is dumped (generally a new filtrate cup is attached) and an elution fluid (typically a buffer at different pH or ionic strength that causes the bound desired component to release from the media) is added and spun through the device in the centrifuge. The eluent in the filtrate cup is collected as it contains the released desired component.

A problem with this type of device is that the volume that can be filtered is limited by the size of the device that can fit within the centrifuge. To filter/capture a large sample such as a liter of serum or tissue culture, one needs to carry out the above process (at least the binding step and often the washing step) multiple times.

An alternative is to use a chromatography column such as a bench scale or preparative column to process the higher volume. Such devices are expensive, and require columns, holders, pumps and sample and filtrate, wash and eluent tanks. Additionally, many of these columns are prepacked with selected media, limiting one's choices of the media available. Further, the capacity of the media used in such columns is typically much greater than what is needed for the amount of material to be captured. This means that one often wastes the extra capacity inherent in the column that is an expensive exercise. Alternatively, one can clean and store the column and use it a second time. This involves a large amount of effort to ensure that the media is fully cleaned so that no residual material (desired or contaminant) from the last run is left behind that might adversely affect the results of the next use of the column. Also most media needs to be kept refrigerated and must be kept from being contaminated during storage.

It would be desirable to provide a device and method for rapid high-quality separations or purifications of samples in a convenient and reliable manner, which can handle sample volumes considerably higher than that handled by conventional centrifugation devices and which effectively uses the correct amount of media and eliminates the need for the washing and storage of columns between runs.

It is therefore an object of the present invention to provide a sample preparation device that can conveniently and rapidly process relatively large volumes of sample, particularly in a single pass with excellent capture.

It is another object of the present invention to provide a sample preparation device that can conveniently and rapidly process relatively large volumes of sample and elute the component of interest at a high concentration factor, greater then 50×.

It is still another object of the present invention to provide a sample preparation device that can conveniently and rapidly process relatively large volumes of sample, without expensive equipment and to provide a system that can reliably process the sample unattended.

It is a still further object of the present invention to provide a sample preparation device that can process relatively large volumes fast enough so as to not require refrigeration.

SUMMARY OF THE INVENTION

The problems of the prior art have been overcome by the present invention, which provides a sample preparation device and method particularly useful for large volume capture and small volume elution. The device of the present invention combines the favorable aspects of both vacuum filtration and centrifugation to provide a low volume (e.g., less than or equal to about 10 mls) of highly purified sample from a large volume (e.g., about 100 mls to 1 liter or more) of sample, such as tissue culture supernatant typically from a hybridoma monoclonal antibody producing cell line.

In one embodiment, the present invention provides a sample preparation device comprising a manifold, a sample holder or reservoir, and a filter unit containing chromatography media such that a filtration path is established between the sample holder, the filter unit and the manifold. Upon subjecting the sample in the sample holder to a driving force such as vacuum, the sample flows from the large reservoir through the chromatography media in the filter unit. Molecules of interest bind to the media and can be washed under vacuum mode. Elution can then be carried out by removing the filter unit and subjecting the media to a driving force such as vacuum or centrifugation and collecting the eluted sample. In another embodiment, molecules of interest can be eluted into a low volume centrifugal spinner directly within the manifold and then further concentrated by centrifugation.

BRIEF DESCRIPTION OF THE DRAWINGS

FIG. 4 is a cross-sectional view of a portion of the sample preparation assembly in accordance with an embodiment of the present invention;

FIG. 5 is a cross-sectional view of a portion of the sample preparation assembly in accordance with another embodiment of the present invention;

FIG. 6 is a perspective exploded view of the underside of the sample holder in accordance with the present invention;

FIG. 7 is a perspective view of the assembled underside of the sample holder in accordance with the present invention;

FIG. 8 is an exploded view of a sample preparation assembly in accordance with an alternative embodiment of the present invention having an ultrafiltration concentrator positioned downstream of the filtration device;

FIG. 9 is a cross-sectional view of the assembly of FIG. 8, shown in an assembled condition;

FIG. 10 is a cross-sectional view of the assembly of FIG. 8 with the ultrafiltration concentrator removed;

FIG. 11 is an exploded view of a sample preparation assembly in accordance with an alternative embodiment of the present invention having a collection tube positioned downstream of the filtration device;

FIG. 12 is a perspective view of the assembly of FIG. 11 in an assembled condition; and FIG. 13 is a cross-sectional view of the assembly of FIG. 11.

DETAILED DESCRIPTION OF THE INVENTION

Figure 1:
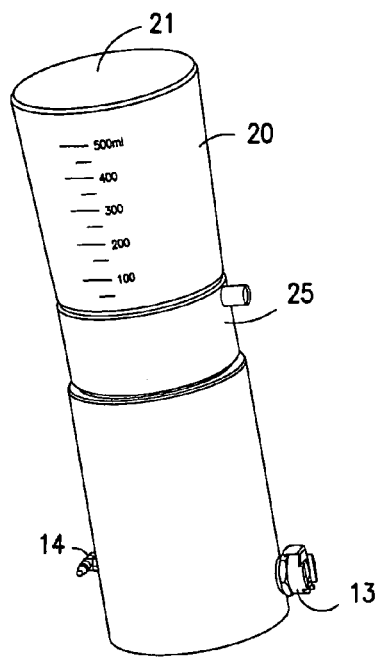
FIG. 1 is a perspective view of the sample preparation assembly in accordance with the present invention.

Turning first to FIG. 1, in accordance with one embodiment of the present invention there is shown a vacuum manifold 12 having a standard connector 13 for connection to a source of vacuum via suitable hosing or the like. The manifold 12 also can include a vent 14. The vent 14 can be used by the researcher to throttle back the flow rate through the filtration device 30 to optimize the sample capture. As can be best seen in FIGS. 4 and 5, the manifold 12 of this embodiment is generally a solid body having an internal bore 15 that is open at the top 15A. The bore 15 communicates through passageway 16 with a driving force such as a vacuum source. The bore 15 also communicates through passageway 17 with vent 14. Preferably the bore 15 is stepped at shoulders 15B and 15C as shown, in order to support a filtration device 30 (as discussed in greater detail below). The manifold 12 is preferably made of a material that is sufficiently rigid and strong to withstand the vacuum applied to the device. Further the manifold material should be compatible with the materials being processed. Suitable materials include metal, ceramics and plastics. Preferably the manifold is made from plastics and more preferably the manifold is made from polyolefins such as polypropylene or polyethylene.

Figure 2:
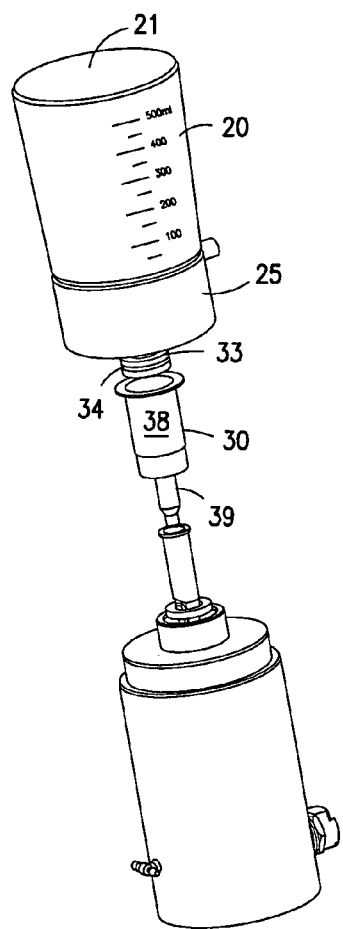
FIG. 2 is an exploded view of the assembly of FIG. 1, having an ultrafiltration device positioned downstream of the separation device.
Figure 3:
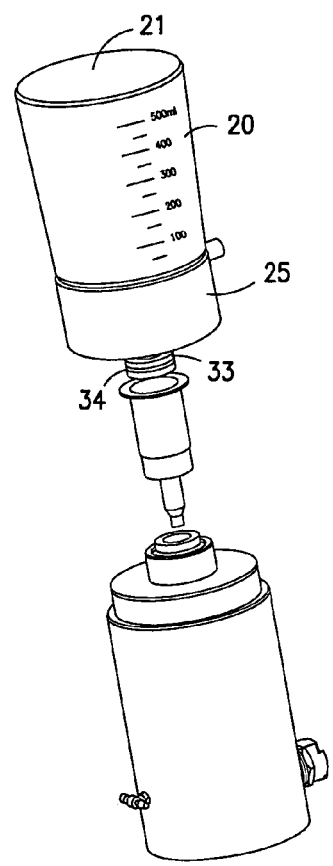
FIG. 3 is a partial exploded view of the assembly of FIG. 1.

Turning back to FIGS. 1-3, the sample holder 20 is a housing having an open top end 21 as shown. In the embodiment shown, the sample holder 20 is a generally cylindrical one-piece housing that can hold relatively large volumes of sample, preferably at least about 50 milliliters, more preferably at least about 100 milliliters, most preferably at least about 500 milliliters. Preferably the sample holder 20 is made of a plastic such as a polyolefin, particularly polypropylene, but is commonly made from polystyrene. The top end 21 preferably has a wide diameter opening in order to facilitate sample transfer into the holder 20. Preferably the sample holder 20 may include a filter 31 such as a membrane and/or glass fibers for pre-filtering the sample in order to minimize or prevent fouling of the chromatography media in the filtration device downstream of the holder 20. This is particularly advantageous where it is desired to re-use the filtration device 30.

The bottom of the sample holder 20 mates with a collar 25. Typically, the collar 25 and holder 20 are bonded together as an integral unit. Bonding can be made by a heat bond, sonic weld, adhesive and the like. The collar 25 is preferably cylindrical, and is configured to mate with the vacuum manifold 12 on annular shoulder 12A (FIG. 4). Collar 25 includes an inner annular ring 26, preferably centrally located in the collar 25, which attaches to the protruding member 27 of the manifold 12. Any suitable means of attachment can be used, such as threads. Preferably the attachment is not permanent, so that the manifold 12 can be re-used with other sample holders and collars. The collar also includes an adaptor 33, best seen in FIGS. 2 and 3. The adaptor 33 is preferably cylindrical and centrally located in the collar 25, preferably circumscribed by inner annular ring 26. It includes a sealing element 34 such as an O-ring, for sealing about filtration device 30. Alternatively, a gasket 36 (FIG. 6) can be used for sealing, which provides a face seal with the open end of the filter unit. The sample holder 20 and collar 25 combination is commercially available from Millipore Corporation and is sold under the Stericup™ or Steritop™ name.

The filtration device 30 is preferably a one-piece housing made from a plastic material such as a polyolefin, particularly polypropylene. It is generally cylindrical, with an upper portion 38 defining a sample chamber, larger enough to contain the required elution volume, that converges to a smaller, generally cylindrical lower portion that contains the chromatography media. The lower portion 39 terminates in a spout 40 defining a fluid outlet for the device.

The device 30 preferably includes chromatography media 45 (FIGS. 4, and 5), the formats of which are not particularly limited. Basically, any media used in peptide and/or protein recovery can be used in this device.

For example, suitable media include functional composite structures comprising resin particles derivatized with functional groups including styrenedivinyl-benzene-based media (unmodified or derivatized with e.g., sulphonic acids, quaternary amines, etc.); silica-based media (unmodified or derivatized with $C_2$, $C_4$, $C_6$, $C_8$, or $C_{18}$ or ion exchange functionalities), to accommodate a variety of applications for peptides, proteins, nucleic acids, and other organic compounds.

Additionally, media formed of polysaccharides such as agarose, crosslinked agarose or dextran or of trisacyrl polymers can be used alone or can be used with various capture chemistries attached to them such as ligands including but limited to Protein A, Protein G, Protein G and the like. Further examples include paramagnetic particles that contain a capture chemistry. Likewise one can utilize controlled pore glass alone or with a ligand such as Protein A (including ProSep®A controlled pore glass media available from Millipore Corporation of Billerica, Mass.).

Those skilled in the art will recognize that a wide variety of matrices with alternative selectivities (e.g., hydrophobic interaction media, ion exchange media, reverse phase media, affinity media (e.g., Protein A, Protein G, Protein L, boronate affinity resins), etc.) also can be used, especially for classes of molecules other than peptides.

Stacked membranes are also suitable as chromatography media. Suitable devices may incorporate a plurality of composite porous structures having materials with different functional groups to fractionate analytes that vary by charge, size, affinity and/or hydrophobicity, and include stacked filters such as glass fiber disc, surface charged membranes or membrane with affinity molecules coupled to the membrane surface.

The term "particles" as used herein is intended to encompass particles having regular (e.g., spherical) or irregular shapes, as well as shards, fibers and powders and optionally including capture chemistries as mentioned above. These particles may be contained between glass, metal or plastic frit or glass mats or plastic nonwovens as is well known in chromatography packing. Alternatively, they may be packed into a chromatography packet that can then be inserted into the device. The filtration device 30 is configured to be slidably received in the bore 15 of the manifold 12. The top rim 37 of the filtration device may include an annular flange that sits on the top shoulder of the manifold 12, as seen in FIGS. 4 and 5. The base of the upper portion 38 of the device 30 seats on a sealing means 46 positioned on shoulder 15B of the manifold 12. Suitable sealing means include an O-ring, flat elastomeric gaskets, or the like, to couple the filtration device 30 and the manifold 12 to create a flow path for the sample. When the device 30 is so positioned in the bore 15 of the manifold, there is sufficient space below the outlet of the device to allow fluid to flow to waste (as in the embodiment of FIGS. 3 and 4), or to allow for the positioning of a second device such as a centrifugal filter unit (as in the embodiment of FIGS. 2 and 5) to further concentrate and desalt the eluted sample, for example. In this latter embodiment, a suitable centrifugal filter unit 60, such as an Amicon® Ultra unit containing an Ultracel® membrane, commercially available from Millipore Corporation, can be used. The centrifuge device is placed below the filter unit after the binding and the washing steps are complete. It is positioned to collect the eluant that may be further concentrated prior to analysis or use.

The flow rate of sample through the device can be controlled in a number of ways. For example, an air leak can be introduced, such as via vent 14 to reduce the vacuum pressure applied to the filter device 30 thereby slowing the flow rate through the device. Alternatively, the packing of the chromatographic media in the filtration device 30, and/or the filter in the sample holder 20, can be modified to control flow.

In operation, the device is assembled with a filtration device 30 positioned in the manifold and the sample holder 20 and collar 25 sealingly positioned over the manifold. Sample is added to the sample holder, and vacuum is applied to the device. The sample flows into the filtration device 30 (preferably after passing through the pre-filter in the sample holder 20), and molecules of interest bind to the media in the filtration device. Molecules that are not of interest pass through the device and are directed to waste or a collection vessel. The bound molecules optionally can then be washed by introducing a suitable wash solution into the sample holder 20, again with the application of vacuum. The filtration device can be removed from the manifold and subjected to further processing, such as centrifugation to elute the molecules of interest.

In another embodiment, a centrifugal device 60 (FIG. 5), such as an ultrafiltration centrifugual device, is positioned in the manifold downstream of the filtration device such as after the bind and wash steps and prior to the elution step. Fluid flowing out of the filtration device is received by the centrifugal device for further processing and analysis.

FIGS. 8-13 illustrate another embodiment wherein the manifold 12' is a bottle or similar housing adapted to be used in communication with a source of vacuum. The sample reservoir 20, (which includes a fitting 44 connectable to a vacuum source), and the filtration device 30, as well as the optional centrifugal device 60, are as described above and are shown in the assembled condition in FIG. 12. The manifold 12' includes a volume sufficient to contain the filtration device 30 and optional centrifugal device 60, as best seen in FIG. 9. In the embodiment shown, the manifold 12' includes an upper lip 62 having external threads 63 for sealingly engaging corresponding inner threads in the inner annular ring 26 of the collar 25. Those skilled in the art will appreciate that other means of sealing attaching the manifold 12' to the holder 20 are within the scope of the present invention. The upper lip 62 has an outer diameter smaller that the outer diameter of the annular flange 31 of the filtration device 30, so that the annular flange 31 can seat on the top surface of the upper lip 62 as shown in FIG. 9. An adapter 33' seals the filtration device 30 to the sample holder 20 as shown.

In the particular embodiment of FIG. 10, the centrifugal device 60 is not used, and filtrate from the filtration device 30 simply collects in the manifold 12'. Depending on the application, this filtrate may be used or discarded.

Suitable materials for the manifold 12' include stainless steel, glass, plastics preferably polyolefins such as polyethylene and polypropylene, but most typically polystyrene.

FIGS. 11 and 13 illustrate an embodiment wherein the eluant from the filtration device 30 is collected in a collection tube 70. The eluted sample so collected can be stored or further processed.

What is claimed is:

1. A sample preparation device, comprising: a sample reservoir, a vacuum manifold having an enclosed volume, and a filter unit positioned in said enclosed volume of said vacuum manifold, said filter unit containing chromatography media and a sample chamber upstream, relative to the direction of fluid flow, of said chromatography media, said sample chamber having a smaller volume than said sample reservoir, whereby said reservoir and manifold are sealingly engaged such that a filtration path is established between the sample reservoir, said filter unit and said manifold.

2. The sample preparation device of claim 1, wherein said filter unit is removable from said manifold and said sample reservoir.

3. The sample preparation device of claim 1, wherein said sample reservoir has a volume of about 50 milliliters.

4. The sample preparation device of claim 1, wherein said manifold comprises a bore, and wherein said filter unit is positioned in said bore downstream from said sample reservoir.

5. The sample preparation device of claim 4, further comprising a centrifugal filtration unit positioned in said bore downstream of said filter unit.

6. The sample preparation device of claim 4, wherein said bore in said manifold is adapted to be in communication with a source of vacuum.

7. The sample preparation device of claim 1, wherein said chromatography media is selected from the group consisting of functional composite structures comprising resin particles derivatized with functional groups and silica-based media.

8. The sample preparation device of claim 1, wherein said chromatography media is selected from the group consisting of functional composite structures comprising one or more layers of derivatized membranes with functional groups or composite membrane structures containing silica-based media.

9. The sample preparation device of claim 1, wherein said sample reservoir includes a filter.

10. The sample preparation device of claim 1, further comprising a vacuum source, and wherein said manifold is a filtrate collection vessel in communication with said vacuum source and said filter unit.

11. The sample preparation device of claim 1, wherein said filter unit is removable from said sample reservoir.

12. A method of purifying a sample, comprising:

providing a sample reservoir in fluid communication with a filter unit comprising chromatography media and a sample chamber, said media being in fluid communication with said sample chamber, said sample chamber being upstream, relative to the direction of fluid flow, of said chromatography media, said sample chamber having a smaller volume than said sample reservoir, said filter unit being positioned in an enclosed volume of a manifold in communication with a vacuum source;

introducing said sample into said sample reservoir;

drawing said sample through said sample reservoir into said filter unit by application of vacuum from said vacuum source to bind molecules of interest to said chromatography media;

removing said filter unit from said manifold; and eluting said molecules of interest from said chromatography media.

13. The method of claim 12, further comprising further processing said eluted molecules of interest by centrifugation.

\* \* \* \* \*